US00PP36591P2

(12) United States Plant Patent
Chen et al.

(10) Patent No.: US PP36,591 P2
(45) Date of Patent: Apr. 8, 2025

(54) ***EPIPREMNUM* PLANT NAMED 'UF-Ea-0310'**

(50) Latin Name: ***Epipremnum* x *aureum***
Varietal Denomination: UF-Ea-0310

(71) Applicant: Florida Foundation Seed Producers, Inc., Marianna, FL (US)

(72) Inventors: Jianjun Chen, Lake Mary, FL (US); Richard J. Henny, Tavares, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 18/955,115

(22) Filed: Nov. 21, 2024

Related U.S. Application Data

(60) Provisional application No. 63/550,135, filed on Feb. 6, 2024.

(51) Int. Cl.
*A01H 5/12* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373
CPC ..... A01H 5/12
See application file for complete search history.

*Primary Examiner* — Kent L Bell
(74) *Attorney, Agent, or Firm* — James R. Holm

(57) ABSTRACT

A new and distinct cultivar of Pothos (*Epipremnun* x *aureum*) plant named 'UF-Ea-0310', particularly distinguished by acuminate leaves with large, irregular bright white center patches, small green-white and greyed-green blotches surrounding the bright white center, followed by dark green coloration extending out to the margin of the leaves, and petioles and stems colored light-yellow.

3 Drawing Sheets

Genus and species: *Epipremnum* x *aureum*.
Cultivar denomination: 'UF-Ea-0310'.

ACKNOWLEDGEMENT OF FEDERAL RESEARCH SUPPORT

N/A.

BACKGROUND OF THE NEW CULTIVAR

*Epipremnum* Schott, commonly known as Pothos, belongs in the family Araceae and is native to the southeast Asian and Solomon Islands in the Pacific. *Epipremnum* has about 10 species, but only *E. aureum* or *E. pinnatum* 'Aureum' (Boyce, 1998) has been widely grown as an ornamental and is among the most popular foliage plants worldwide. Pothos is an important foliage plant in the commercial trade. Based on the USDA Floriculture Crops Statistics, the wholesale value of Pothos in 2018 was $22.89 million. It ranked as the third among all cultivated foliage plant genera. With the increased popularity of "living walls" since 2010, pothos has been the highest in-demand indoor foliage plant, especially demand for cultivars with contrasting and bright foliage colors. Prior to 2009, there have been only four cultivars available in commercial trade, 'Golden Pothos' (unpatented), 'Marble Queen' (unpatented), 'Jade' (unpatented), and 'Neon' (unpatented). In 2009, two new Pothos cultivars were released namely, 'UFM10' (U.S. Plant Pat. No. 20,930, commercial name Green Genie™) and 'UFM12' (U.S. Plant Pat. No. 21,217, commercial name Pearls and Jade®). These two cultivars are the result of mutation breeding through exposure to gamma ray radiation. In 2022, three new Pothos cultivars were released namely, 'UF-Ea-0311' (U.S. Plant Pat. No. 35,875), 'UF-Ea-0316' (U.S. Plant Pat. No. 35,876), and 'UF-Ea-0317' (U.S. Plant Pat. No. 35,874). These Pothos cultivars were developed through direct in-vitro somatic cell embryogenesis from leaf explants.

Pothos has bisexual flowers like its relatives *Anthurium* and *Spathiphyllum* but rarely flowers in nature. Prior to the present disclosure, there have been no literature reports of Pothos breeding through hybridization. Gibberellic acid ($GA_3$) is known to stimulate flowering in many flowering plant species. Molecular analysis has shown that transcripts for the biosynthesis of $GA_3$, EaGA3ox1 and $GA_3$-responsive floral meristem gene, EaLFY were inactive in Pothos. Thus, exogenous application of $GA_3$ has shown to induce Pothos flowering. After the induction of flowering, pollen can be collected and transferred to the stigmas of the same flower (self-pollination) or to that of a different flower (cross-pollination) to produce seed.

SUMMARY OF THE INVENTION

The invention relates to a new and distinct cultivar of Pothos plant named 'UF-Ea-0310'. In 2010, 'Marble Queen' plants were grown vertically on poles in a greenhouse in Apopka, Florida. After six months of growth, $GA_3$ at 2,500 mg/L was sprayed on the entire plant until runoff. Flowers were induced. Pollen was collected and placed on stigmas using a brush. After seeds formed, the seeds were collected and immediately sown onto a substrate. 'UF-Ea-0310' was selected from the resulting self-pollinated progenies based on leaf shape and leaf variegation patterns as well as stem color and growth form.

First asexual propagation of 'UF-Ea-0310' occurred in Apopka, Florida in September 2011; since then, it has been asexually propagated through single or double eye stem or vine cuttings for 24 or more generations.

Plant Breeder's Rights for the new cultivar 'UF-Ea-0310' have not been applied for, and 'UF-Ea-0310' has not been made publicly available more than one year prior to the filing date of this application.

The new cultivar 'UF-Ea-0310' has not been observed under all possible environmental conditions. The phenotype of the new cultivar may vary with variations in environment and cultural practices such as temperature, light intensity, fertilization, irrigation, and application of plant growth regulators without any change in genotype.

The following are the most outstanding and distinguishing characteristics of 'UF-Ea-0310' when grown under normal horticultural practices in Apopka, Florida: acuminate leaves with large, irregular bright white center patches, small green-white and greyed-green blotches surrounding the bright white center, followed by dark green coloration extending out to the margin of the leaves, and petioles and stems colored light-yellow.

When compared to the parent and commercial Pothos cultivar 'Marble Queen', leaves of 'UF-Ea-0310' are acuminate in shape, whereas leaves of 'Marble Queen' are cordate in shape. Additionally, leaves of 'UF-Ea-310' have a solid bright white center coloration, whereas leaves of 'Marble Queen' have a broad mottled coloration consisting of green, yellow and white. Further, stems of 'UF-Ea-310' are colored light-yellow, whereas stems of 'Marble Queen' are colored dark-green.

DESCRIPTION OF THE FIGURES

This new Pothos cultivar 'UF-Ea-0310' is illustrated by the accompanying photographs, which show the plant's form and foliage. The colors shown are as true as can be reasonably obtained by conventional photographic procedures. The photographs are of seven-month-old plants grown from unrooted cuttings in November 2018 in a shaded greenhouse in Apopka, Florida.

DETAILED BOTANICAL DESCRIPTION OF THE CULTIVAR

Figure 1:
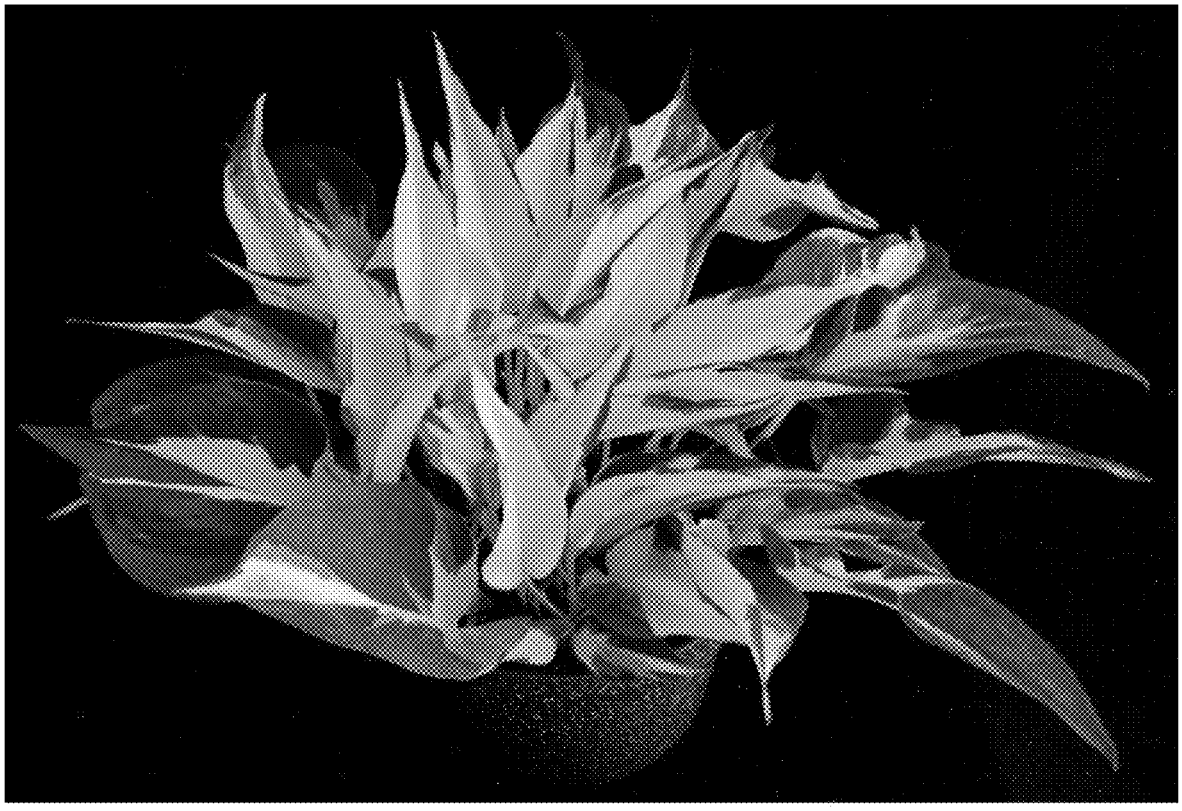
FIG. 1 shows the growth habit, form, and foliage of the new Pothos cultivar UF-Ea-0310.
Figure 2:
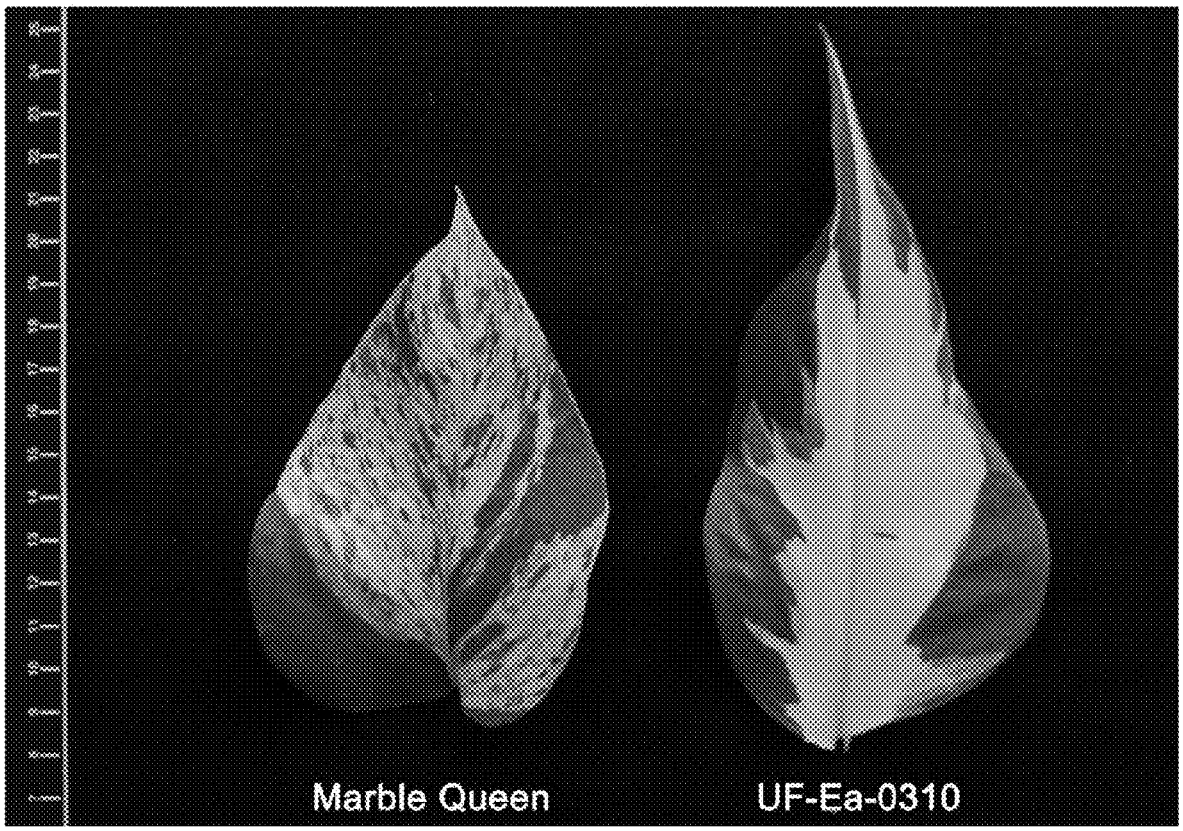
FIG. 2 shows a side-by-side comparison of the adaxial surface of a leaf of 'UF-Ea-0310' (right) and 'Marble Queen' (left)
Figure 3:
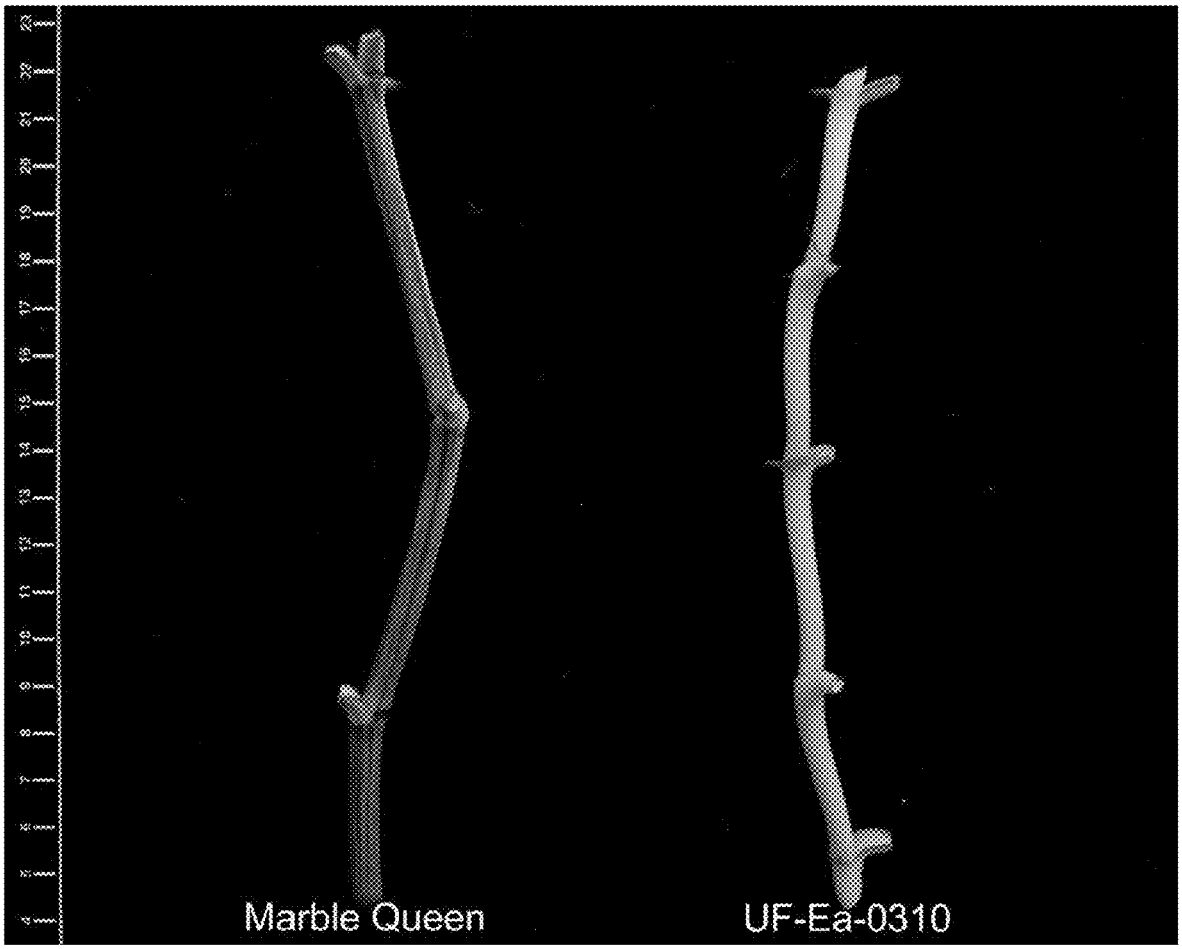
FIG. 3 shows a side-by-side comparison of a stem of 'UF-Ea-0310' (right) and 'Marble Queen' (left).

Foliage color was determined under full sun conditions in the middle of the day in a shaded greenhouse with 75% light exclusion. Color references are to The R.H.S. Colour Chart of The Royal Horticultural Society of London (R.H.S.), 1995 Edition. The following detailed description of 'UF-Ea-0310' was obtained using seven-month-old plants grown from unrooted cuttings in November 2018 in a shaded greenhouse in Apopka, Florida. The plants were propagated in mist for 21 days after cuttings were stuck, then grown in 20 cm (8 in) diameter pots with approximately 15 cuttings per pot for approximately 3-4 additional weeks.

BOTANICAL DESCRIPTION

Botanical classification:

*Family*.—Araceae.

*Botanical name*.—*Epipremnum* x *aureum*.

*Common name*.—Pothos.

*Cultivar*.—'UF-Ea-0310'.

Plant description:

*Plant type*.—Perennial tropical vine.

*Growth habit*.—Compact and trailing.

*Height from soil level to top of foliar plane*.—Approximately 24 cm.

*Growth rate*.—Medium.

*Branching characteristics*.—One main stem (vine), no lateral branching.

*Vine length*.—Approximately 25 cm on a 3-month-old stem.

*Vine diameter*.—Approximately 0.7 cm.

*Internode length*.—4.2 cm.

*Texture of vines*.—Glabrous and smooth.

*Shape of vines*.—Predominantly round and slightly flattened on one side.

*Color of vines*.—Light yellow (4A).

*Number of leaves per vine*.—6 to 8 on a 3-month-old vine.

Propagation:

*Type of cuttings*.—Vegetative stem cuttings having at least 1 node.

*Time to initiate roots*.—21 days.

*Time to produce a rooted cutting*.—20 weeks after root establishment.

*Root habit*.—One aerial root oriented downwards and present at each basal node, aerial roots produce fine roots when in contact with the soil.

*Root description*.—Aerial roots are 1-4 cm in length and 1-2 mm in diameter, colored brown (165A), soil main roots are about 1.2 mm in diameter and fine roots are about 0.3 mm in diameter and colored white (NN155D).

Foliage description:

*Arrangement*.—Alternate.

*Attachment*.—Petiolate.

*Leaf*.—Shape: Acuminate. Length: 14.5 cm. Width: About 7.0 cm. Apex shape: Acuminate. Base shape: Truncate to slightly cordate. Texture (upper surface): Glabrous and leathery. Texture (lower surface): Glabrous and leathery. Orientation: Newer leaves are held erect and upwards, mature leaves are held erect and horizontal Margins: Entire, undulating and slightly folded downwards at the edges. Color: On mature leaves, bright white (NN155D), green-white (157A), greyed-green (189B), and green (137A) in irregular patches; young and recently expanded leaves often appear light-yellow (157D) with a green 137A margin; variegation is visible on both the adaxial and abaxial surfaces, but the greyed-green (189B) may not be visible on the abaxial side of older leaves. Leaf sheen (both upper and lower surfaces): Shiny Venation: Pattern: Eucamptodromous. Color: Upper surface: White (NN155D), green-white (157A), greyed green (189B), and green (137A). Lower surface: White (NN155D), green-white (157A), and green (137A).

*Petiole*.—Length: 6-10 cm. Width: Approximately 0.4 cm. Color: Light yellow (4A).

Inflorescence: None observed to date.

Fruit and seed set: None observed to date.

Disease and insect resistance: None observed to date.
Cold tolerance: Tolerant down to 5° C.
Drought tolerance: Tolerant.

COMPARISON WITH KNOWN CULTIVARS

When compared to 'UFM12' (U.S. Plant Pat. No. 21,217, commercial name "Pearls and Jade"®), the new cultivar 'UF-Ea-0310' is also compact but has larger leaves that are acuminate in shape, whereas 'UFM12' has smaller leaves that are aristate in shape. Additionally, 'UF-Ea-0310' has a broad center leaf coloration of white, whereas 'UFM12' has a center leaf coloration of green-white to greyed-green in irregular sized patches. Further, 'UF-Ea-0310' has stems that are predominantly light yellow, whereas 'UFM12' has stems that are predominantly green with white streaking.

What is claimed is:

1. A new and distinct *Epipremnum* plant named 'UF-Ea-0310' as illustrated and described herein.

* * * * *